United States Patent [19]

Nakano et al.

[11] Patent Number: 5,302,521
[45] Date of Patent: Apr. 12, 1994

[54] PROCESS FOR PRODUCING L-LYSINE BY IODOTHYRONINE RESISTANT STRAINS OF MUCORYNEBACTERIUM GLUTAMICUM

[75] Inventors: Tetsuo Nakano; Tomoki Azuma; Yoshiyuki Kuratsu, all of Hofu, Japan

[73] Assignee: Kyowa Hakko Kogyo Co., Ltd., Tokyo, Japan

[21] Appl. No.: 962,273

[22] Filed: Oct. 16, 1992

[30] Foreign Application Priority Data

Oct. 21, 1991 [JP] Japan .................................. 3-272461

[51] Int. Cl.$^5$ .......................... C12P 13/08; C12N 1/20
[52] U.S. Cl. ................................... 435/115; 435/252.1
[58] Field of Search .............................. 435/115, 252.1

[56] References Cited

U.S. PATENT DOCUMENTS

| 3,708,395 | 1/1973 | Nakayama et al. | 435/115 |
| 4,169,763 | 10/1979 | Nakayama et al. | 435/115 |
| 4,657,860 | 4/1987 | Nakanishi et al. | 435/115 |

FOREIGN PATENT DOCUMENTS

| 597387 | 1/1988 | Australia . | |
| 0327945 | 8/1989 | European Pat. Off. | 435/115 |
| 2601035 | 12/1989 | France | 435/115 |

Primary Examiner—Marian Knode
Attorney, Agent, or Firm—Fitzpatrick, Cella, Harper & Scinto

[57] ABSTRACT

A process for producing L-lysine by fermentation includes the steps of culturing a microorganism belonging to the genus Corynebacterium having a resistance to iodothyronine in a nutrient medium to form and accumulate L-lysine in the resulting culture and recovering the L-lysine therefrom.

2 Claims, No Drawings

PROCESS FOR PRODUCING L-LYSINE BY IODOTHYRONINE RESISTANT STRAINS OF MUCORYNEBACTERIUM GLUTAMICUM

BACKGROUND OF THE INVENTION

The present invention relates to a process for producing L-lysine by fermentation.

L-lysine is one of the essential amino acids, which is widely used for various purposes such as for the preparation of medicines, additives to feedstuffs and foodstuffs and the like.

Heretofore, as processes for producing L-lysine by fermentation using a microorganism belonging to the genus Corynebacterium, there have been known processes of using strains having a nutritional requirement for various amino acids such as homoserine (U.S. Pat. No. 3,708,395), strains having a resistance to S-(2-aminoethyl)-L-cysteine (U.S. Pat. No. 3,708,395), strains having a resistance to an aspartic acid analogue or a sulfur drug (U.S. Pat. No. 4,169,763), strains having a resistance to $\beta$-naphthoquinoline (FR-A-2,601,035), strains having a resistance to a purine analogue or a pyrimidine analogue (U.S. Pat. No. 4,657,860) and strains having a resistance to an iturin-related substance (EP-A-0,327,945).

As a result of various studies for obtaining strains having an improved L-lysine productivity in view of recently increased demand for L-lysine, it has been found that a strain having a resistance to iodothyronine has a remarkably improved ability to produce L-lysine.

SUMMARY OF THE INVENTION

The present invention relates to a process for producing L-lysine which comprises culturing an L-lysine-producing microorganism belonging to the genus Corynebacterium and having a resistance to iodothyronine in a culture medium to form and accumulate L-lysine in the culture, and recovering the resultant L-lysine therefrom.

DETAILED DESCRIPTION OF THE INVENTION

Iodothyronine as used herein denotes thyronine substituted with iodine and includes L-form, D-form and a mixture thereof. The preferred example of the iodothyronine are 3,3',5,5'-tetraiodothyronine, 3,3',5-triiodothyronine, 3,5-diiodothyronine and the like. Further, a sodium salt and a potassium salt, of the iodothyronine are also included in the definition of iodothyronine.

As the microorganism used in the present invention, any microorganism may be used so long as it belongs to the genus Corynebacterium and has a resistance to iodothyronine and an ability to produce L-lysine.

The L-lysine-producing microorganism having a resistance to iodothyronine can be obtained by endowing a resistance to iodothyronine with an L-lysine-producing strain. Alternatively, the desired mutant can be obtained by imparting nutrient auxotrophy, a drug-resistance, etc. for endowing L-lysine productivity, to the strain having a resistance to iodothyronine, which is derived from a wild strain.

The mutation may be induced in the conventional manner such as irradiation of ultraviolet rays, the treatment with chemicals such as N-methyl-N'-nitro-N-nitrosoguanidine.

The desired mutant may be selected from strains subjected to the mutation treatment by picking up from mutants grown on a suitable medium, for example, a minimal agar plate medium containing iodothyronine at a concentration sufficient to inhibit the growth of the parent strain, a mutant having L-lysine-producing ability greater than that of the parent strain.

In the production of L-lysine using the desired mutant of the present invention, any conventional method for culturing bacteria is applicable.

Any of synthetic medium and natural medium may be used as the medium for the present invention, so long as it properly contains a carbon source, a nitrogen source, inorganic materials and other nutrients required for the growth of the microorganism utilized.

As the carbon source, various carbohydrates such as glucose, fructose, sorbitol, glycerol, sucrose, starch, starch hydrolyzate, molasses, fruit juice, etc., organic acids such as acetic acid, fumaric acid, lactic acid, citric acid, etc., and alcohols, such as ethanol, methanol, etc., may be used.

As the nitrogen source, ammonia, inorganic and organic ammonium salts such as ammonium chloride, ammonium sulfate, ammonium acetate, ammonium phosphate, etc., urea, amines, other nitrogen-containing materials and peptone, meat extract, yeast extract, corn steep liquor, casein hydrolyzate, soybean meal acid hydrolyzate, various microbial cells, digest of microbial cells, etc., may be used.

As the inorganic materials, potassium dihydrogen phosphate, dipotassium hydrogen phosphate, magnesium phosphate, magnesium sulfate, sodium chloride, ferrous sulfate, manganese sulfate, copper sulfate, calcium carbonate, etc., may be used. When a microorganism to be used in the present invention requires specific nutrients for growth, an appropriate amount of the nutrients is added to the medium. In some cases, these nutrients are added as components of the natural substances exemplified as the nitrogen source.

Further, the productivity of L-lysine by the present microorganism can be, in some cases, enhanced by adding other various additives, for example, vitamines such as biotin, thiamine, nicotinic acid, $\beta$-alanine, pantothenic acid, etc., various antibiotics, amino acids such as valine, cysteine, leucine, aspartic acid, glutamic acid, etc., to the medium.

Culturing is carried out under aerobic conditions, for example, by shaking culture, agitation submerged culture, etc., at a temperature of 20°~40° C., preferably 28°~36° C. and at a pH of 5~9, preferably around neutral.

The pH of the medium is adjusted with calcium carbonate, acid or alkali solution, ammonia, pH buffering agent, etc. Usually, after culturing for 1 to 7 days, L-lysine is formed and accumulated in the resulting culture.

After the completion of culturing, precipitates, such as cells, are removed from the culture and L-lysine can be recovered from the culture by use of the conventional methods, such as ion-exchange resin treatment, concentration, adsorption, salting-out in combination.

Practice of specific embodiments of the invention is illustrated by the following representative examples.

EXAMPLE 1

Preparation of a Mutant Having a Resistance to Iodothyronine:

*Corynebacterium glutamicum* H-4934 (FERM BP-1655) having a resistance to thialysine, rifampicin, streptomycin, 6-azauracil, β-naphthoquinoline and an iturin-related substance was subjected to the following mutation treatment.

The cells of the H-4934 strain were suspended in a buffer solution containing 250 μg/ml of N-methyl-N'-nitro-N-nitrosoguanidine at a temperature of 30° C., for 30 minutes. The cell suspension was spread onto a minimal agar plate medium having the following composition and further containing sodium salt of 3,3',5-triiodo-L-thyronine (hereinafter referred to as "TIT" at a concentration of 50 μg/ml. Such concentration was sufficient to inhibit the growth of the H-4934 strain.

After culturing at 30° C. for 3 days, the grown colonies were separated as a mutant having a resistance to TIT, and subjected to the L-lysine production test to select the desired mutant having L-lysine-producing ability greater than that of the parent strain. Among the thus selected mutants was *Corynebacterium glutamicum* H-8241.

For the purpose of examining the growth degree against TIT, H-8241 strain and H-4934 strain each were suspended in a sterilized water and the suspension was spread onto a minimal agar plate medium having the following composition, and further containing TIT in a concentration shown in Table 1, so that the cell density might be $1 \times 10^4$ cells/cm$^2$. After culturing at 30° C. for 5 days, the growth degree was observed. The results are shown in Table 1.

*Corynebacterium glutamicum* H-8241 has been deposited as of Oct. 8, 1991 with the Fermentation Research Institute, Agency of Industrial Science and Technology 1-3 Higashi 1 chrome Tsukabashi Ibaraki-ken 305 Japan under the Budapest Treaty and has been assigned a deposition number of FERM BP-3594.

Composition of the Minimal Agar Plate Medium glucose 10 g/l, NH$_4$Cl 8 g/l, urea 2 g/l, KH$_2$PO$_4$ 1 g/l, K$_2$HPO$_4$ 3 g/l, MgSO$_4$.7H$_2$O 0.4 g/l FeSO$_4$.7H$_2$O 10 mg/l, MnSO$_4$.4H$_2$O 10 mg/l, ZnSO$_4$.7H$_2$O 1 mg/l, CuSO$_4$.5 H$_2$O 1 mg/l, biotin 50 μg/l, nicotinic acid 5 mg/l and agar 20 g/l, pH 7.3.

TABLE 1

| Strain | TIT (μg/ml) | | |
|---|---|---|---|
| | 0 | 10 | 30 |
| H-4934 | ++ | + | − |
| H-8241 | ++ | ++ | ++ |

++: sufficient growth,
+: growth to some extent,
−: no growth.

EXAMPLE 2

L-Lysine Production Using the Mutant of the Present Invention

*Corynebacterium glutamicum* H-4934 an H-8241 each were inoculated in 10 m/l of a seed medium having the following composition in a 300 m/l-Erlenmeyer flask, and cultured at 32° C. for 24 hours with shaking.

Composition of the Seed Medium sucrose 50 g/l, peptone 20 g/l, yeast extract 5 g/l, (NH$_4$)$_2$SO$_4$ 8 g/l, KH$_2$PO$_4$ 1 g/l, KH$_2$HPO$_4$ 1 g/l, MgSO$_4$.7H$_2$O 0.5 g/l, biotin 50 μg/l, thiamine hydrochloride 3 mg/l, urea 1 g/l, CaCO$_3$ 10 g/l, pH 7.2.

Then 3 ml of the seed culture was inoculated into a 30 ml of a production medium having the following composition in a 300 ml-Erlenmeyer flask and cultured at 32° C. for 72 hours with shaking.

Composition of the Production Medium sucrose 100 g/l, yeast extract 5 g/l, (NH$_4$)$_2$SO$_4$ 50 g/l, KH$_2$PO$_4$ 1 g/l, MgSO$_4$.7H$_2$O 0.5 g/l, FeSO$_4$.7H$_2$O 10 mg/l, MnSO$_4$.4H$_2$O 10 mg/l, biotin 300 μg/l, urea 2 g/l, CaCO$_3$ 30 g/l, pH 7.2.

After completion of the culturing, the amount of L-lysine accumulated in the culture was colorimetrically determined according to the acidic copper-ninhidrin method [Chinard. F. D., *Journal of Biological Chemistry* 199, 91 (1952)].

The results are shown in Table 2.

TABLE 2

| Strain | L-lysine hydrochloride (mg/ml) |
|---|---|
| H-4934 | 44 |
| H-8241 | 48 |

One thousand milliliters of the culture obtained by culturing H-8241 strain was centrifuged (3000 rpm, 10 minutes) and the pH of the resultant supernatant was adjusted to 1.5 with sulfuric acid. The thus obtained supernatant was passed through a column packed with strongly acidic ion exchange resin, Diaion SK-1B (H+-form, trademark of Mitsubishi Kasei Corporation) to adsorb L-lysine thereon.

After washing the column with water, elution was effected with 2N aqueous ammonia to collect L-lysine-containing fractions. The collected fractions were concentrated, and the pH of the concentrate was adjusted to 5.5 with hydrochloride. The resultant concentrate was cooled while adding ethanol thereto to thereby obtain 38 g of a crystal of L-lysine.

What is claimed is:

1. A process for producing L-lysine which comprises the steps of:
   culturing *Corynebacterium glutamicum* FERM BP-3594 in a culture medium;
   accumulating L-lysine in the culture medium; and
   recovering said L-lysine therefrom.

2. A biologically pure culture of *Corynebacterium glutamicum* FERM BP-3594.

* * * * *

UNITED STATES PATENT AND TRADEMARK OFFICE
CERTIFICATE OF CORRECTION

PATENT NO. : 5,302,521
DATED : April 12, 1994
INVENTOR(S) : TETSUO NAKANO, ET AL.

It is certified that error appears in the above-indentified patent and that said Letters Patent is hereby corrected as shown below:

On the title page, item [54] and column 1, line 4, "MUCORYNEBACTERIUM" should read --CORYNEBACTERIUM--.

COLUMN 1

Line 47, "example" should read --examples--.

COLUMN 2

Line 66, "salting-out" should read --or salting-out--.

COLUMN 3

Line 4, "Iodothyronine:" should read --Iodothyronine--;

Line 18, " "TIT" " should read --"TIT")--;

Line 40, "Technology" should read --Technology,--;

Line 41, "1 chrome Tsukabashi" should read --1 chome Tsukaba-shi--; and "Japan" should read --Japan,--; and Line 48, "0.4 g/l" should read --0.4 g/l,--.

UNITED STATES PATENT AND TRADEMARK OFFICE
CERTIFICATE OF CORRECTION

PATENT NO. : 5,302,521
DATED : April 12, 1994
INVENTOR(S) : TETSUO NAKANO, ET AL.

It is certified that error appears in the above-indentified patent and that said Letters Patent is hereby corrected as shown below:

COLUMN 4

Line 5, "an" should read --and--; and
Line 7, "300 m/l-Erlenmeyer" should read --300 ml-Erlenmeyer--.

Signed and Sealed this

Second Day of May, 1995

BRUCE LEHMAN

Attest:

Attesting Officer        Commissioner of Patents and Trademarks